United States Patent [19]

Woods et al.

[11] 4,426,329

[45] Jan. 17, 1984

[54] ONE STEP MODIFICATION AND OXIDATION OF WAXES

[75] Inventors: John H. Woods, Longview; Charles E. Laughlin, Gladewater, both of Tex.; Toby R. Graves, Tulsa, Okla.

[73] Assignee: Petrolite Corporation, St. Louis, Mo.

[21] Appl. No.: 288,852

[22] Filed: Jul. 31, 1981

[51] Int. Cl.$^3$ .................... C07C 53/00; C07C 27/10
[52] U.S. Cl. .................................... 260/398.6; 208/3
[58] Field of Search ..................... 260/398.6; 208/3

[56] References Cited

U.S. PATENT DOCUMENTS

| | | | |
|---|---|---|---|
| 1,981,384 | 11/1934 | Friedolsheim | 260/398.6 |
| 2,794,040 | 5/1957 | Annable | 260/398.6 |
| 2,798,841 | 7/1957 | Fish | 208/3 |

*Primary Examiner*—John F. Niebling
*Attorney, Agent, or Firm*—Sidney B. Ring; Leon Zitver

[57] ABSTRACT

This invention relates to a one step process of oxidizing a natural or synthetic non-benzenoid hydrocarbon wax in the presence of a metal oxide or hydroxide, such as potassium, sodium or lithium oxide or hydroxide, and to the product formed by such oxidation.

12 Claims, No Drawings

ONE STEP MODIFICATION AND OXIDATION OF WAXES

This invention relates to a novel, simple, and convenient method for making modified oxidized hydrocarbon waxes and their derivatives.

In the realm of oxidized waxes, it is known that a wide variety of products can be obtained from the oxidation of treated petroleum waxes, for example, microcrystalline waxes obtained by separation and purification of crude tank bottom petroleum settlings. However, the method generally followed in previous work is limited to microcrystalline or paraffin waxes and involves two steps: pretreatment in an inert atmosphere with an alkali at high temperature, and subsequent oxidation of the treated wax in the same or different vessel. U.S. Pat. No. 2,798,841, dated July 9, 1957, describes such a process.

The pretreatment prescribed in U.S. Pat. No. 2,798,841 requires a temperature of 250°–270° C. (482°–518° F.) and an inert atmosphere to prevent flashing. The oxidation phase requires transfer of the pretreated material to a separate vessel unless the high temperature required in pretreatment can be attained in a vessel designed for air oxidation. The time required for pretreatment is 10–30 hours and 6–30 hours for oxidation; total batch time is 16–60 hours.

Four disadvantages of such a procedure are: two steps are required (pretreatment and oxidation), the high temperature of pretreatment, the length of time allocated to complete the process, and the alkali used in pretreatment is limited to potassium hydroxide and a narrow range of concentration.

Another method of producing modified oxidized waxes comprises the two step process of oxidizing wax to the oxidized product and then treating the oxidized product with alkali. (Conventional Process).

We have now discovered a new and improved technique for preparing modified oxidized non-benzenoid hydrocarbon waxes that avoids the multiple steps of the conventional process and reduces the total reaction time of the conventional process. In addition, it avoids high temperatures and multiple processing steps and significantly reduces the total time of the process described in U.S. Pat. No. 2,798,841.

We have also broadened the type of alkali and alkali metal concentration used in U.S. Pat. No. 2,798,841.

We have also employed a range of waxes which is broader than employed in U.S. Pat. No. 2,798,841.

Accordingly, we have found that the alkali treatment and oxidation can be accomplished simultaneously via a one step process in a non-inert atmosphere, at a temperature within the range of about 93° C. to about 232° C. (200°–450° F.), such as from 240°–380° F., but preferably from 300°–340° F., and within about 5 to about 18 hours. Such reactions can be carried out in a vessel generally constructed with stainless steel lining and equipped with heating/cooling coils and an air sparging system designed to also function as the agitator.

The amount of alkali to be added can vary from about 12 acid number equivalents to about 50 acid number equivalents, such as from 13 to 35 acid number equivalents, but preferably from 15 to 30 acid number equivalents. We have also found that even though potassium hydroxide is the preferred alkali, other alkalis of metals in Group IA of the Periodic Table of the elements such as lithium hydroxide and sodium hydroxide are effective in making the desired modified oxidized wax. An additional discovery we have made is that the starting material is not necessarily limited to microcrystalline or paraffinic waxes, but can be chosen from among natural and synthetic waxes such as the higher molecular weight alpha-olefins, for example, Gulf's $C_{30+}$Alpha Olefin, and high molecular weight hydrocarbon polymer waxes, for example Allied Chemical's AC-6 and South Africa's Paraflint.

In the production of these modified oxidized waxes, the point at which the reaction is terminated is determined by the alkalinity of said wax whereby a small sample of approximately 1 gram is dissolved in 100 milliliters of a xylene/1-propanol mixture (40% xylene by volume) and refluxed with about 3 milliliters of dilute HCl for about 30 minutes and then titrated with potassium hydroxide (or other suitable base) to a phenolphthalein end point. The alkalinity of the product is expressed in milligrams of potassium hydroxide per gram sample of wax. The reaction termination is then based on an alkalinity of greater than about 1, such as about 2 to about 8, and preferably not exceeding 11.

The waxes produced by this invention are comparable to those made by the two step process of U.S. Pat. No. 2,798,841. When subjected to heating in the presence of water, these waxes will gradually thicken as their melting point is approached and will become like jelly as heating continues at that temperature. This "thermo thickening" is a primary characteristic of these waxes and is probably due to ionic or partial ionic bonding created between the wax and its residual alkali content and activated by water and heat.

The waxes of this invention are similar to those produced by first oxidizing the starting wax and then reacting with a Group IA base metal. However, the products of this invention are lighter in color than those made by oxidation and then base reaction.

In summary, (1) U.S. Pat. No. 2,798,841 treats the wax with alkali to form an intermediate product which is then oxidized (2 steps);

(2) Conventional oxidation oxidizes the wax to form the oxidized product which is then treated with alkali (2 steps).

In contrast, the present invention oxidizes wax in the presence of alkali in a one step process.

These processes may be summarized as follows:

|  |  |  | Process Time | Product Color |
|---|---|---|---|---|
| Present One Step Process | Wax + Alkali + $O_2$ 240–380° F. | → Final Product | 5–18 hrs | tan |
|  | Step 1 | Step 2 |  |  |

-continued

| | | | | | | Process Time | Product Color |
|---|---|---|---|---|---|---|---|
| (1) U.S. Pat. No. 2,798,841 2 step process | Wax + alkali + N$_2$ $\xrightarrow[482-518° \text{ F.}]{}$ | Intermediate Product | $\xrightarrow[240-380° \text{ F.}]{O_2}$ | Final Product | | 16–60 hrs | tan |
| | Step 1 | | Step 2 | | | | |
| (2) Conventional Process | Wax $\xrightarrow[240-380° \text{ F.}]{O_2}$ | Oxidized Product + alkali | $\xrightarrow[200-300° \text{ F.}]{\text{heat}}$ | Final Product | | 16–60 hrs | brown |

The following examples are presented for purposes of illustration and not of limitation.

The procedure of Example 1 is typical of the general procedures employed in subsequent examples of this invention.

EXAMPLE 1

9.0 pounds of POLYWAX ®655 was charged in its molten state to a 2½ inch diameter by a 7 foot long oxidizer equipped with a top inserted sparger that has its lower end within 6 inches of the oxidizer bottom when fully inserted and is attached to an air feed line regulated by a 40 cfh air flow rotometer. The oxidizer is also equipped with an air inlet at the bottom of the oxidizer that is attached to an air line regulated by a 20 cfh air flow rotometer. This bottom air inlet is provided to agitate the alkali and keep it dispersed throughout the reaction mixture. This is necessary since the alkali has a tendency to sink to the bottom of the oxidizer where it cannot react with the molten wax. To the molten wax which was held at 160° C. (320 ° F.) and agitated by air introduced at 20 cfh at the bottom and 20 cfh through the top sparger was added 318 grams of 45% potassium hydroxide (35 acid number equivalents). The reaction was terminated after 24 hours. The final alkalinity was 11, the softening point (ASTM D-36) was 204° F., and the penetration at 77° F. (ASTM 1321-55T) was 4.

The alkali in this and subsequent examples is added in solution rather than in solid form as in U.S. Pat. No. 2,798,841 which makes for much better alkali dispersion. However, either procedure for addition of the base will produce an acceptable product.

EXAMPLE 2

In a manner similar to Example 1, 9.0 pounds of POLYWAX ®655 having a melting point (ASTM D-127) of 98° C. (209° F.) and penetration at 25° C. (77° F.) of 2 was reacted with 109 grams of 45% potassium hydroxide (12 acid number equivalents) that was added over a period of one hour to the wax held at 162° C. (325° F.) and agitated by air introduced to the vessel at 10 cfh at both top and bottom. The reaction was allowed to continue for 18 hours at which time the vessel was drained based on an alkalinity of 4. The product so obtained had a softening point 97° C. (206° F.) and penetration at 25° C. of 2 and also exhibited thermo thickening.

EXAMPLE 3

In like manner, 9.0 pounds of POLYWAX ®655 was reacted with 159 grams of 45% potassium hydroxide (17.5 acid number equivalents) that was added over a 20 minute period to the molten wax held at 160° C. (320° F.) and agitated by air introduced at 10 cfh at both top and bottom. The reaction was allowed to continue for 24 hours at which time the vessel was drained based on an alkalinity of 3. The product obtained had a softening point of 97° C. (206° F.) and 25° C. penetration of 4 and also exhibited thermo thickening.

EXAMPLE 4

In like manner, 9.0 pounds of POLYWAX ®655 was reacted with 227 grams of 45% potassium hydroxide (25 acid number equivalents) that was added over 35 minutes to the molten wax held at 168° C. (335° F.) and agitated by air introduced at 20 cfh at both top and bottom. The reaction continued for 19 hours and the vessel was drained based on an alkalinity of 2. The product had a softening point of 96° C. (205° F.) and 25° C. penetration of 3 and also exhibited thermo thickening.

EXAMPLE 5

In like manner, 9.0 pounds of POLYWAX ®655 was reacted with 272 grams of 45% potassium hydroxide (30 acid number equivalents) that was added over 105 minutes to the molten wax held at 171° C. (340° F.) and agitated by air introduced at 20 cfh at both top and bottom. The reaction continued for 25 hours and the vessel was drained based on an alkalinity of 4. The product had a softening point of 99° C. (210° F.) and 25° C. penetration of 3 and also exhibited thermo thickening.

EXAMPLE 6

Similarly, 10.0 pounds of BARECO ®C-1035 was reacted with 217 grams of 45% potassium hydroxide (21.5 acid number equivalents) that was added over 25 minutes to the molten wax held at 320° F. and agitated by air introduced at 4 cfh at the top and 20 cfh at the bottom. The reaction continued for 21 hours and the vessel was drained based on an alkalinity of 5. The product had a softening point of 197° F. and 25° C. penetration of 4 and also exhibited thermo thickening.

A key test to determine the quality of the product of this invention is to emulsify the product according to any of several standard emulsification procedures. One of these procedures follows:

EXAMPLE A 48 grams of Gulf C$_{30+}$Alpha Olefin is added to 352 grams of the product to be tested and the mixture is heated to 104° C. (220° F.). A solution of 27 grams iso-propyl alcohol and 63 grams water is heated to 77° C. (170° F.) and added slowly to the melted wax mixture while allowing the temperature to decrease to 88° C. (190° F.). To this mixture is added 0.9 grams of Tween 60. One fourth liter of water is then heated to 66° C. (150° F.) and added slowly to the mixture while allowing the temperature to drop to between 74° C.

(165° F.) and 77° C. (170° F.). At the end of this addition, 286 milliliters of cold water is added. The temperature should then be between 60° C. (140° F.) and 63° C. (145° F.). The mixture is stored when the temperature falls to about 38° C. (100° F.).

EXAMPLE 7

In the manner of Example 1, 8.9 pounds of South African Paraflint H1 having a melting point (ASTM D-127) of 110° C. (230° F.) and 25° C. (77° F.) penetration of 3 was reacted with 194 grams of 45% potassium hydroxide (21.5 acid number equivalents) that was added over 50 minutes to the molten wax held at 143° C. (290° F.) and agitated by air introduced at 10 cfh at both top and bottom. The temperature was raised to 166° C. (330° F.) after one hour and held there for 17 hours. The vessel was then drained based on an alkalinity of 6. The final product had a softening point (ASTM D-36) of 100° C. (212° F.) and 25° C. penetration of 1 and also exhibited thermo thickening.

EXAMPLE 8

In like manner, 9.1 pounds of Gulf $C_{30+}$Alpha-Olefin having a melting point of 78° C. (172° F.) and 25° C. (77° F.) penetration of 13 was reacted with 196 grams of 45% potassium hydroxide (21.5 acid number equivalents) that was added over 15 minutes to the molten wax held at 162° C. (325° F.) and agitated by air introduced at 20 cfh at the top and 10 cfh at the bottom. The temperature was reduced at 1½ hours to 149° C. (300° F.) and held for 20 hours. It was then raised to 166° C. (330° F.) for 3⅜ hours at which time the vessel was drained based on an alkalinity of 9. The product had a softening point of 77° C. (171° F.) and 25° C. penetration of 13 and also exhibited thermo thickening.

EXAMPLE 9

In like manner, 8.9 pounds of POLYWAX®2000 having a melting point of 127° C. (260° F.) and 25° C. (77° F.) penetration of 0.5 was reacted with 193 grams of 45% potassium hydroxide (21.5 acid number equivalents) that was added over 25 minutes to the molten wax held at 166°0 C. (330° F.) and agitated by air at 20 cfh at the top and 10 cfh at the bottom. The reaction continued for 47 hours and the vessel was drained based on an alkalinity of 9. The final product had a melting point of 124° C. (256° F.) and 25° C. penetration of 0.5 and also exhibited thermo thickening.

EXAMPLE 10

In like manner, 8.9 pounds of CITGO Pacemaker 45 having a melting point of 71° C. (160° F.) and 25° C. (77° F.) penetration of 15 was reacted with 194 grams of 45% potassium hydroxide (21.5 acid number equivalents) that was added over 20 minutes to the molten wax held at 166° C. (330° F.) and agitated by air introduced at 20 cfh at the top and 10 cfh at the bottom. The reaction was terminated at 26 hours based on an alkalinity of 6. The product had a softening point of 73° C. (163° F.) and 25° C. penetration of 14 and also exhibited thermo thickening.

EXAMPLE 11

In like manner, 8.9 pounds of Allied Chemical AC-6 having a melting point of 100° C. (212° F.) and 25° C. (77° F.) penetration of 6 was reacted with 157 grams of 45% potassium hydrooxide (17.5 acid number equivalents) that was added over 10 minutes to the molten wax held at 160° C. (330° F.) and agitated by air introduced at 20 cfh at the top and 10 cfh at the bottom. The temperature was lowered at 4½ hours to 149° C. (300° F.) and held for 17½ hours. It was then raised to 171° C. (340° F.) for 3 hours. The reaction was stopped at 28 hours based on an alkalinity of 8. The product had a softening point of 98° C. (208° F.) and 25° C. penetration of 6 and also exhibited thermo thickening.

EXAMPLE 12

In like manner, 9.0 pounds of a 50/50 blend of Allied Chemical AC-6 (melting point and penetration as per example 11) and BARECO®BE SQUARE®195 WHITE (melting point of 91° C. (195° F.) and penetration at 25° C. of 6) having a melting point of 98° C. (209° F.) and 25° C. penetration of 6 was reacted with 159 grams of 45% potassium hydroxide (17.5 acid number equivalents) that was added over 5 minutes to the molten wax held at 171° C. (340° F.) and agitated by air introduced at 20 cfh at the top and 10 cfh at the bottom. The air flow was changed to 40 cfh at the top and 20 cfh at the bottom at the 5 hour mark and held for 45 minutes. The vessel was drained based on an alkalinity of 10 at 5¾ hours. The final product had a softening point of 92° C. (198° F.) and 25° C. penetration of 3 and also exhibited thermo thickening.

Other examples which demonstrate the broader range of alkali and the similarity between these and the above products and a salt of an oxidized wax are outlined below.

EXAMPLE 13

In like manner, 9.0 pounds of BARECO®C-1035 having a melting point of 93° C. (200° F.) and a 25° C. penetration of 5 was reacted with 125 grams of 45% sodium hydroxide (22 acid number equivalents) that was added to the molten wax held at 154° C. (310° F.) and agitated by air introduced at 12 cfh at the top and 10 cfh at the bottom. The reaction was stopped at 9½ hours based on an alkalinity of 4. The product had a softening point of 93° C. (200° F.) and 25° F. penetration of 4. This product also exhibited thermo thickening. This product was able to be emulsified using the procedure detailed in Example A.

EXAMPLE 14

To a 3-neck 1000 ml flask was added 479 grams of oxidized BARECO®C-1035 that had a 9 acid number, a melting point of 91° C. (195° F.), and 25° C. penetration of 8. To the molten wax held at 116° C. (240° F.) and agitated under a nitrogen blanket was added 23 grams of 45% potassium hydroxide (21.5 acid number equivalents) that was added over 15 minutes. The reaction was allowed to continue under a continuous nitrogen blanket and was terminated at 23 hours. The product had an alkalinity of 3, a softening point of 90° C. (194° F.) and 25° C. penetration of 5. This product has all the characteristics and properties of the product of Example 6 except it is darker in color. The product of this example has similar physical properties, has the same alkalinity and forms an equivalent emulsion when processed according to the procedure of Example A, demonstrating that our one step process produces products equivalent to those of a conventional oxidation with subsequent base treating except that one process produces lighter colored products. Although we do not wish to be bound by theoretical considerations, a probable explanation of this is that in the present invention the Group IA base reacts with the wax acids in an oxidizing environment whereas in the process described in Example 14, the base reacts in a reducing environment. The oxidizing environment either retards or destroys the color bodies, whereas the reducing environment promotes color body formation.

In summary, this invention relates to a process of oxidizing non-benzenoid hydrocarbon waxes in the presence of a sufficient amount of a metal of Group IA of the periodic Table and at a temperature capable of yielding a final alkalinity of at least about 1, but preferably 2 to 8.

The non-benzenoid hydrocarbons have a molecular weight of from about 300 to 5000, such as from about 325 to 4000, but preferably from about 350 to 3000, and having a melting point of from about 110° F. to 300° F., such as from about 120° F. to 290° F., but preferably from about 140° F. to 270° F.

A wide variety of hydrocarbon waxes can be employed including natural and synthetic waxes, for example, microwax, paraffin wax, Fisher-Tropsch wax, polyethylene, linear polyethylene, alpha-olefins, etc.

The metals employed to prepare the salts are from Group IA of the Periodic Table such as sodium, potassium, lithium, etc., but preferably potassium.

These are generally employed as alkalis of such metals, i.e., as the hydroxides or oxides.

In contrast to the 2-step process of U.S. Pat. No. 2,798,841 the present process is a one-step process, thus reducing total reaction time.

The products of this invention are similar to but lighter in color than the product of the conventional 2-step process of oxidation followed by treatment with the basic metal.

We claim:

1. A one step process which comprises oxidizing a natural or synthetic non-benzenoid hydrocarbon wax having, prior to oxidation, a molecular weight of about 300 to 5000 and a melting point of about 110° F. to 300° F., said process consisting essentially of (1) adding about 12 to 50 acid number equivalents of a Group IA metal oxide or hydroxide to said wax; and (2) oxidizing the wax at about 200° F. to 450° F. for at least five hours and terminating the oxidation when the product has an alkalinity of greater than about 1.

2. The process of claim 1 where the Group IA metal is sodium.

3. The product of claim 2.

4. A one step process which comprises oxidizing a natural or synthetic non-benezenoid hydrocarbon wax having, prior to oxidation, a molecular weight of about 300 to 5000 and a melting point of about 110° F. to 300° F., said process consisting essentially of (1) adding about 12 to about 50 acid number equivalents of a Group IA metal oxide or hydroxide to said wax; and (2) oxidizing the wax at about 200° F., for at least five hours and terminating the oxidation when the product has an alkalinity of about 1 to about 11.

5. The process of claim 4 where the group IA metal is sodium.

6. The product of claim 5.

7. The process of claim 1 where the Group IA metal is potassium.

8. The process of claim 1 where the Group IA metal is lithium.

9. The process of claim 4 where the Group IA metal is potassium.

10. The process of claim 4 where the Group IA metal is lithium.

11. The product of claim 8.

12. The product of claim 10.

* * * * *